United States Patent [19] [11] 4,373,027

Berneman et al. [45] Feb. 8, 1983

[54] MICROPARTICLES, PREPARATION THEREOF AND APPLICATIONS THEREOF IN BIOLOGY, PARTICULARLY IN THE CULTURE OF HUMAN DIPLOID CELLS

[76] Inventors: Armand Berneman, 11, Rue de Crussol, 75011 Paris; Alain David, Rue de Rollet-Cuise la Motte, 60350 Berneuil sur Aisne; Florian Horaud, 2, rue Albert de Mun, 92190 Meudon; Emile Segard, Village du Parc Rimbertlieu-Villers sur Coudun, 60150 Thourotte, all of France

[21] Appl. No.: 213,314

[22] Filed: Dec. 5, 1980

[30] Foreign Application Priority Data

Dec. 5, 1979 [FR] France ................................ 79 29910

[51] Int. Cl.[3] ......................... C12N 5/00; C12N 5/02; C12M 3/00; C12M 3/04

[52] U.S. Cl. .................................... 435/240; 435/241; 435/284; 435/285; 435/286

[58] Field of Search ............... 435/240, 241, 284, 285, 435/286

[56] References Cited

U.S. PATENT DOCUMENTS 4,036,693 7/1977 Levine et al. ........................ 435/241
4,189,534 2/1980 Levine et al. ........................ 435/241
4,266,032 5/1981 Miller et al. ......................... 435/241
4,293,654 10/1981 Levine et al. ........................ 435/241

OTHER PUBLICATIONS

William B. Jakoby and Ira H. Pastan, editors, Methods In Enzymology, vol. LVIII, pp. 266, 267 and 576–578, 1979 (3/2/79).

*Primary Examiner*—Robert J. Warden

[57] ABSTRACT

These microparticles are formed, at least on their surface, from a reticulated protein. (FIG. 1).

48 Claims, 2 Drawing Figures

MICROPARTICLES, PREPARATION THEREOF AND APPLICATIONS THEREOF IN BIOLOGY, PARTICULARLY IN THE CULTURE OF HUMAN DIPLOID CELLS

BACKGROUND OF THE INVENTION

The invention relates to novel microparticles, the preparation thereof and the applications thereof in biology, especially in the culture of animal, and in particular human, diploid cells, normal or infected for example by a virus or a parasite.

It is known that normal diploid cells which are cells of embryonic origin are used for elaborating different products of cellular origin, such as interferons, or else for culture of viruses suitable for the manufacture of viral vaccines for human use.

But the production of these cellular elements on an industrial scale is difficult due to the requirements for the culture of normal diploid cells. In fact, contrary to transformed cells, which are capable of developing in suspension in a liquid medium, so with a satisfactory yield, normal diploid cells can only multiply on a solid support.

Single layer culture on a solid support of a large quantity of cells in Roux boxes or in rollers requires a large number of containers, which constitutes a limiting factor and has proved unusable for commercial purpose. Research has been carried out with respect to solid carriers for carrying out cultures adaptable to mass culture conditions in fermentation tanks.

Microparticles or beads, in general in the form of microbeads of a diameter of about 40 to 200 μm have more particularly attracted attention for this purpose. They allow in fact substantially homogeneous cultures to be carried out adaptable in principle to culture conditions in a fermenter. They have furthermore the advantage of offering a large culture surface, which allows an increase in the produced cell yield.

However, microbeads known up to present do not entirely satisfactorily resolve the particular problems of adherence, multiplication, toxicity, met with in the culture of normal or infected human diploid cells.

Now, the work carried out in this field by inventors has established that particular microcarriers, especically for the culture of diploid cells allowing an extremely satisfactory adherence and growth of cells on their surfaces, could be elaborated from some types of proteins used for the formation at least of their surfaces.

The invention relates then to novel microparticles favoring, because of their composition and the properties which result therefrom, the adherence and the growth of human diploid cells.

It also relates to a process for preparing these microparticles.

In accordance with another aspect, the invention relates to the application of these microparticles to the culture of cells, more particularly normal human diploid cells, and to the culture of infected diploid human cells or with the in situ infection thereof in view.

SUMMARY OF THE INVENTION

The microparticles, in accordance with the invention, to be designated without distinction also by the term microcarriers or else microbeads, are characterized in that they are formed from particles of which at least the surface is formed by a reticulated protein, this protein being chosen from those capable of forming a gel, i.e. a visco-elastic mass giving rise, after reticulation, to a fibrous-type mass reticulated into a mesh.

These particles have advantageously a charge capacity of about 0.5 to 1.8 meq per gram of dry particles. Preferably, the charge capacity of these microbeads is from 0.9 to 1.6 meq/gram and advantageously of $1\pm0.3$ meq per gram of dry particles.

In a remarkable way, the microbeads complying with the above-defined characteristics prove particularly efficient as microcarriers for the culture of human diploid cells and this, even with aged cellular cultures already having undergone several passages, i.e. having given rise to several generations.

In the rest of the description, reference will be more particularly made to human diploid cells, considering the quite particular interest which the invention assumes for their culture. But it is clear that the invention also applies with advantage to cultures of animal diploid cells.

The protein, present at least at the surface of these microbeads, forms a precious carrier for the adherence of cells and the multiplication thereof.

In accordance with a preferred embodiment of the invention, the protein entering into the composition of the microbeads and forming at least the surface thereof is formed by gelatin.

It is known that gelatin is a product from the partial hydrolysis of collagens. Depending on the method of manufacture thereof, a distinction is made between the gelatin obtained by the acid process, having an isoelectric point pHi between 7 and 9 and that obtained by the alkaline process having a pHi between 4.7 and 5.

These two types of gelatin may be used within the scope of the invention, the gelatin obtained by the alkaline process having the advantage, because of its surface tension properties, of spreading out more easily while giving rise to a substantially homogeneous surface, more suitable for the contemplated biological applications, as microcarriers.

In another embodiment of the invention, the protein entering into the composition of the microbeads is formed by fibronectine. This is a protein of the fibrinogen type, having a molecular weight of about 440,000 present in plasma and at the surface of different cells. This protein is described particularly in Proc. Natl. Acad. Sci. USA, Vol. 76 No. 6 p. 2644–2648, June 1979, by S/A/ Santoro and L. W. Cunningham.

In accordance with the invention, the proteins entering into the composition of the microbeads are reticulated. The reticulation agent is advantageously chosen from conventional reticulation agents. Use is more specially made of a multifunctional agent having at least two aldehyde, azo, sulfonic acid, fluoro groups activated by reactive nitro, imine azide or chloro groups connected with cyclic structures having a suitable resonance.

Because of its efficiency and its availability, glutaraldehyde is advantageously used.

With the purpose of using the microparticles of the invention as microcarriers for cellular cultures, so as to obviate the possible risks of toxicity, with respect to the cells, the functional groups of the recticulation agent, not engaged in the reticulation action, are blocked.

The blocking of the functional groups in question is effected advantageously with the help of the protein entering into the composition of the microbeads.

In accordance with a variation of the invention, the microbeads are formed essentially by the reticulated protein, preferably by the recticulated gelatin such as mentioned above, or else by reticulated fibronectine.

According to another variation of the invention, the microbeads contain the reticulated protein at their surface, in the form of a coating.

Such microballs are preferably formed of particles comprising a coating of reticulated protein fixed on an anchoring nucleus.

An appropriate nucleus is formed from a material having chemical groups capable of reacting with the functional groups of the protein of the coating while giving rise to a link and having a density allowing the particles to be maintained in suspension in a culture medium.

As preferred material of this type, use is made of reticulated dextran such as the one commercialized under the trademark Sephadex by Pharmacia Fine Chemicals, Inc. substituted by tertiary or quaternary amino groups, in a proportiion such that the charge capacity of the particle before coating is of the order of 0.5 to 1.8 meq per gram of dry Sephadex, preferably from 0.9 to 1.6 and advantageously $1\pm0.3$ meq per gram of dry Sephadex.

It will be noted that the charge capacity of the protein-coated particles is substantially of the same order of size.

The amino groups are more specially formed by diethylaminoethyl (DEAE) or diethyl-2-hydroxy-propylaminoethyl (QAE).

For preparing the microcarriers of the invention, a solution, advantageously aqueous, is formed of a protein having the above-defined characteristics, in a concentration for obtaining particles having the desired properties considering their biological applications.

This solution is then treated so as to form particles constituted entirely by the protein in question or, according to a variation, comprising this protein in the form of a coating.

To elaborate the protein particles, the protein solution is treated so as to form particles, preferably droplets having a diameter of the order of 40 to 200 μm, particularly by pulverizing it in a bath consisting, for example, of a mixture of vegetable oil, n-butyl alcohol and glutaraldehyde in suitable concentrations for the mass setting of the droplets. The protein solution may also be caused to flow through a capillary tube.

As for the protein coating, it is advantageously obtained by contacting said protein solution with a suspension, preferably aqueous, of particles having a diameter of the order of 40 to 200 μm, formed from a material capable of forming an anchoring nucleus for the protein coating such as defined above. Such a material having a low charge capacity is advantageously prepared in accordance with the technique described in U.S. Pat. No. 1,777,970. The operating conditions, particularly temperature, duration, pH, being chosen depending on the products used, the coating and the charge capacity desired.

Experience shows that a satisfactory coating is obtained by operating at a pH close to 7 and at a temperature greater than the ambient temperature, advantageously less than 40° C., a suitable reaction time then being of the order of 24 hours. To promote contact of the particles with the protein, the reaction mixture is advantageously subjected to agitation. The protein particles, or particles covered with protein, obtained are washed then placed in contact with a solution, also advantageously aqueous, of the reticulation agent.

The optimum temperature, duration and concentration conditions are finalized in routine operations so as to obtain the particles having the desired characteristics depending on the protein and the reticulation agent used.

As already pointed out, the free functions of the reticulation agent are blocked.

After the reticulation step, the particles are advantageously washed and then placed in contact with a solution, preferably aqueous, of the protein of the microball, and this under conditions allowing the desired blocking to be achieved.

An electronic microscopic examination of the microbeads thus obtained shows that they have a surface having the appearance of a lattice-work.

Work carried out on these microbeads has shown that, unexpectedly, they allow extremely satisfactory adherence and multiplication of normal human diploid cells.

It is also possible to infect, with a virus or a parasite, the cells which have grown on the microbeads, which allows viruses, or parasites, to be prepared.

The microbeads of the invention are then advantageously used as microcarriers in cellular cultures, more specially of normal or infected human diploid cells.

The invention relates then also to a culture process for human diploid cells comprising use of the above-defined microbeads.

In a preferred embodiment of this process, a sterile suspension of the microbeads in question is formed in a medium suitable for the culture and the growth of normal human diploid cells. This medium is seeded under sterile conditions with the diploid cells, then it is subjected to incubation under temperature and duration conditions allowing satisfactory multiplication of the cells.

The seeding step is advantageously carried out by using the human diploid cells at the rate of about $10^5$ cells per ml of culture medium for about 1 to 2 mg of microbeads per ml of culture medium and preferably for 1.5 to 1.7 and more especially about 1.6 mg of microbeads.

The seeding step is also advantageously carried out by using the human diploid cells at the rate of $2.5\times10^5$ cells per ml of culture medium for 4 mg of microbeads per ml of culture medium.

The culture medium in which the microbeads are in suspension is preferably brought up to the temperature which will then be used during the incubation step.

During this incubation step, it is important to offer the cells the maximum of surface of the beads. The seeded medium is then advantageously agitated to make it homogeneous. It is then left to sediment so as to allow contact of the cellular mass with the microbeads with a view to the adhesion of cells. Finally, it is slightly agitated to ventilate the cellular layer-microbead interface.

A preliminary treatment of the microbeads used as microsupports in the culture process of the invention allows favorably a better cellular growth.

A suitable treatment comprises at least a step for sterilizing the microbeads in a phosphate buffer called "PBS". These sterile microbeads are then preincubated in complete culture medium to which there is possibly added lactalbumin hydrolysate. This culture medium comprises all the elements required for the growth of the cells and will be used in the incubation step carried out after seeding.

This preincubation step is advantageously effected at a temperature between ambient temperature and about 40° C., preferably at 37° C. and, under these conditions, for about 24 hours in the presence of lactalbumin hydrolysate.

It is also preferable, before preincubation, to subject the microparticles to a sterilization step. The sterilization may be effected by using as suspension medium the washing buffer, to which there is possibly added the protein entering into the composition of the microparticles.

Afterwards, the microparticles are rinsed with PBS and they are preincubated in a Dulbecco culture medium containing possibly lactalbumin hydrolysate, in the case where the microparticles are subsequently seeded with human diploid cells. All these operations take place naturally in a sterile way.

The growth steps effected bring out the precious qualities of the microcarriers used in accordance with the invention.

As is shown by the results given in the following examples, their efficiency appears remarkable not only insofar as the rate of adhesion of the cells is concerned but also as far as cellular division is concerned.

It can in fact be seen with interest that the percentage of adhesion of the cells on the microcarriers with respect to the initial number of cells added to the culture flask is extremely satisfactory and reaches values of the order of 80%, 24 hours after seeding.

This strong adhesion of the cells at the beginning of the culture is advantageously followed by high multiplication of these cells on the microcarriers.

The number of cell divisions observed after 5 to 7 days of culture proved in fact to be greater than 2.

Advantageously, the work carried out shows moreover that the cells grown on the microcarriers of the invention may be used again in a fermenter having a large volume, which shows the viability of the cells.

Such results make possible the use of the process of the invention particularly in the large-scale production of viruses with a view to preparing viral vaccines or other cellular products such as interferons.

DESCRIPTION OF THE DRAWINGS

Other characteristics and advantages of the invention will appear from the examples which follow with reference to the accompanying drawings in which.

DESCRIPTION OF THE PREFERRED EMBODIMENTS

Example 1

Figure 1:
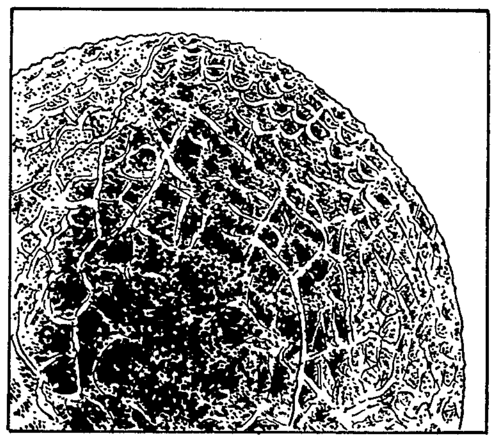
FIG. 1 shows an electronic microscope photograph of a microparticle covered with a gelatin coating.

Preparation of Sephadex-DEAE microbeads covered with reticulated gelatin

These microbeads are prepared using the three following steps (a) to (c), in which:

(a) DEAE groups are grafted onto the Sephadex microbeads, (b) the Sephadex-DEAE beads obtained are covered with gelatin, (c) reticulation of the gelatin and blocking of the functional groups from the reticulation agent are carried out.

Each of these steps are carried out as follows:

(a) Grafting of the DEAE groups on the Sephadex microbeads.

Reticulated dextran microbeads commercialized by the Company PHARMACIA under the trademark Sephadex, of the type medium G 50, are allowed to swell in water, then they are washed several times with distilled water. A suspension of 50 g of these microbeads in 500 ml of distilled water is then formed. A 500 ml aqueous solution is prepared containing 0.5 mole of diethylaminoethyl chloride and 0.75 mole of NaOH, another DEAE halide, such as bromide, and/or another alkaline hydroxide, such as KOH, may be used. The pH of this solution is greater than 11. This solution is added to the microbead suspension in a reactor thermostatically controlled to 60°±1° C. The mixture is agitated within the medium with a stainless-steel propeller having 4 blades placed perpendicularly. The reaction is allowed to continue for 30 to 80 minutes depending on the tests carried out. The reaction mixture is cooled by adding a volume of cold distilled water so as to stop the grafting.

It is allowed to decant and the matter floating on the surface is removed. This operation is repeated several times so as to eliminate the reagents, particularly the DEAE, and to obtain a pH equal to 7.

The charge capacity of the microballs thus obtained is checked. For this purpose the chloride anions exchanged with the microbeads are measured. The microbeads are washed first of all with a solution of 0.1 N hydrochloric acid so as to saturate the exchange sites with $Cl^-$ ions, then they are washed with a $10^{-4}$ N solution of HCl, to remove the nonfixed choride ions and finally with a 10% w/v solution of sodium sulfate so as to displace the chloride anions with sulfate anions. After this washing the solution is collected which is titrated with a 1 M silver nitrate solution using potassium chromate as indicator.

The measurements carried out show that the microbeads obtained have a charge capacity per gram of dry G 50 Sephadex of about 0.9 to 1.6 meq.

(b) Coating of the microbeads with gelatin

To 100 ml of gelatin obtained by the alkaline process, such as the limed bone gelatin 240 BLS commercialized by the firm ROUSSELOT, Paris, France, at 10% w/v, there is added 200 ml of a suspension containing 10 g of microbeads such as obtained in step (a).

This solution, having a pH close to 7, is maintained at 37° C. for 24 hours with weak agitation. After 24 hours, the beads are washed several times with distilled water to eliminate the excess gelatin.

(c) Reticulation of the gelatin and blockage of the functional groups from the reticulation agent.

The beads are placed again in suspension in 200 ml of distilled water then 20 ml of glutaraldehyde in a 25% aqueous solution are added.

The mixture is kept at ambient temperature for 24 hours and with weak agitation.

After 24 hours, the beads are washed several times with distilled water to eliminate the excess glutaraldehyde. The absence of reagent in the floating matter resulting from washing is checked by measuring the optical density at 280 nm (adsorption wavelength of glutaraldehyde).

The free functions of the glutaraldehyde are then blocked with gelatin.

The microbeads are then taken again in 200 ml of distilled water and 100 ml of gelatin at 10% are added.

This solution is maintained at 37° C. for about 10 hours. To eliminate the free excess gelatin present in the floating matter, the microbeads are then washed (several times) with distilled water.

In FIG. 1, there is shown an electronic microscope photograph of microbeads thus prepared. It can be seen that the recticulated gelatin coating forms a fine net at the surface of the microbeads.

Example 2

Treatment of the microbeads obtained in Example 1 with a view to their application as microcarriers for cellular cultures The microbeads are washed first of all 5 to 6 times with PBS. Then a suspension of these microbeads in PBS, containing possible 3 to 4% gelatin, is placed in an autoclave at 120° C. for 20 minutes, in a humid vapor.

Example 3

Use of the microbeads treated in accordance with Example 2 as microcarriers for cellular culture Before proceeding with the seeding step, the microbeads treated in accordance with Example 2 are washed with a culture medium called Dulbecco medium, prepared in the laboratory, to which lactalbumin hydrolysate is added and if necessary antibiotics. This Dulbecco medium is described particularly in "International Association of Microbiological Societies Permanent Section of Microbiological Standardization", Minutes of the Seventh Meeting of the Committee on Cell Cultures, a conference which was held in Geneva on Sept. 14, 1970, edited by Professor Hayflick and Dr. Perkins, p. 123–124, published in 1971. After the third washing, the microbead suspension is incubated at 37° C. for 12 hours.

At the time of testing, after decantation, a suspension fraction containing 1.6 to 5 mg/ml is taken and placed sterilely in a 250 to 1000 ml flask of the spinner type. The microbeads are left to decant then they are rinsed twice with 10 ml of Dulbecco medium to which is added 10% of aseptic calf serum coming from Medical and Veterinary Supplies, Slough, GB. The volume is completed to 100 ml or 150 ml or 500 ml or 1 liter, depending on the volume of the flask.

The suspension preheated to 37° C. is sterilely seeded with human foetal lung cells MRC 5 obtained from the 27th to 32nd passage.

The cells come from a deep-frozen stock prepared in the laboratory, complying with international standards. The cell culture is treated with a 0.25% trypsin dispersant solution. The cells are counted and added to the culture flask in a proportion of about $10^5$ cells for 1.6 mg of microbeads per ml of suspension. After seeding, the culture medium is left at 37° C. for two hours under agitation, then the agitation system is started up.

So as to check the adhesion of the cells, the first day and the growth the following days, 1 ml of microball suspension is taken each day.

The cells are counted as follows. The suspension taken is decanted then rinsed once with a trypsin: versene volume for volume mixture (1.25°/$_{oo}$:0.1°/$_{oo}$ final concentrations). Then they are subjected to incubation at 37° C. in the presence of 1 ml of the trypsin: versene mixture.

After 5 to 10 minutes, the suspension is subjected to agitation then isotonic liquid is added of the same density as the cells. After sedimentation of the beads, the cells are counted in the floating matter with a Coulter counter sold by Coultronics. The pH of the medium is measured and adjusted regularly with a 5.5% bicarbonate solution. The cellular growth is estimated in accordance with two parameters, namely:

(1) percentage adhesion of the cells on the microcarriers with respect to the initial number of cells added to the culture flask;

(2) the maximum number of cells obtained after 5 to 7 days culture, which allows the number of cellular divisions to be calculated.

There is obtained, 18 hours after the subculture cells having adhesion percentages on average greater than 30–40% and reaching 80 to 90%. As to the number of divisions obtained, it is generally greater than 2 and may reach, operating under the conditions described above, values close to 3.

The trend of the growth curves of the cells on the microbeads of the invention shows the appearance of a plateau, which represents the maximum density of the cells, about the sixth day after seeding or depending on the tests the seventh or eighth day.

Figure 2:
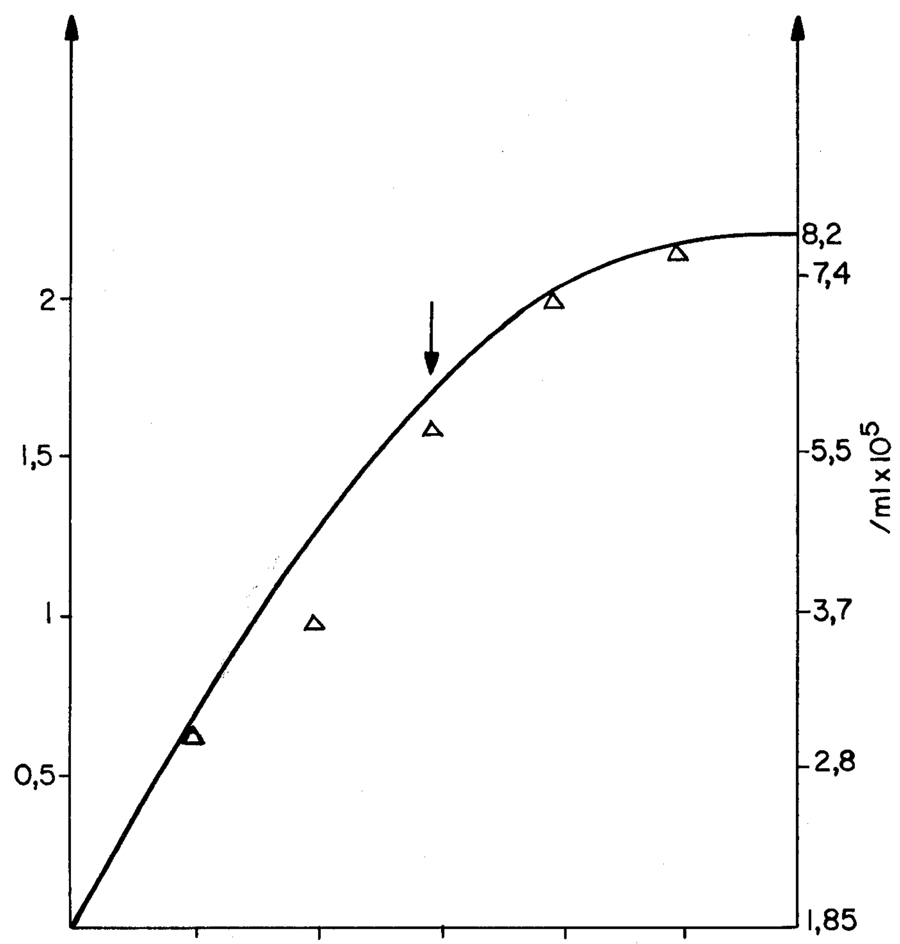
FIG. 2 shows the growth curve of a cell culture of an MRC-5 strain on microcarriers in accordance with the invention.

There is shown in FIG. 2 the growth curve of MRC-5 cells on Sephadex G 50 DEAE microbeads coated with gelatin, having a charge capacity of 1.1 meq per gram of dry and nontreated Sephadex G 50. The growth test was carried out in a volume of 100 ml with 4 mg/ml of microbeads having undergone the pretreatment described in Example 2, without use of gelatin and $2.5\times10^5$ cells.

A change of medium was carried out 4 days after the beginning of the test so as to eliminate the metabolites always rejected into the medium and thus to maintain growth. The growth curve on which there is shown as abscissa the duration of the test, expressed in days, and as ordinates the number of cell divisions, has the appearance of a normal curve obtained in a monolayer culture system. The appearance of a plateau can be seen about the sixth day corresponding to cell divisions greater than 2.

Comparative Example 3A

Comparative growth tests were carried out for MRC-5 cells coming from the 28th to 32nd passage on microbeads of the invention, on the one hand, and on microbeads of the prior art not coated with reticulated gelatin.

As microbeads of the prior art, Sephadex G 50 DEAE type microbeads (reticulated dextran on which DEAE groups are grafted) were used having a charge capacity of the order of 1.5 meq/g of Sephadex G 50. By way of comparison, in accordance with the invention, Sephadex G 50 DEAE microballs were used coated with reticulated gelatin and prepared as in Example 1, having a charge capacity of 1.6 meq/g of dry Sephadex G 50.

In these comparative tests, the microbeads are subjected to a pretreatment such as described in Example 2, in which the microbeads are washed with PBS then they are placed in an autoclave, in a PBS medium.

The seeding step is carried out as in Example 3. Beads and cells are used in respective concentrations of 4 mg/ml and $2.5\times10^5$/ml of culture medium.

A practically zero growth was observed with the microbeads not coated with a reticulated protein and more particularly gelatin whereas the number of generations obtained with the microbeads of the invention is equal to 2.

As far as the adhesion rate is concerned, it can be seen that it is of the order of 45 in the case of the invention and close to 60 with the microbeads of the prior art.

These results show the advantageous effect procured by the microbeads of the invention whose inherent characteristics enable the MRC-5 cells used in these tests, which are aged cells which have been subjected to a great number of passages, to strongly adhere and to multiply.

EXAMPLE 4

Study of the growth of MRC-5 cells having grown on microcarriers of the invention Several passages of MRC-5 cells were effected over microcarriers of the invention formed from type G 50 DEAE Sephadex, covered with gelatin having a charge capacity of 1.3 meq/g of Sephadex (before seeding, the microcarriers were washed with PBS, then incubated for 30 minutes in PBS containing 3% w/v gelatin and finally placed in an autoclave at 120° C. for 30 minutes in the presence of gelatin).

The cells were detached then, in 100 ml flask, they were reseeded on their old support, the respective concentrations being $2.8\times10^5$ cells/ml of culture medium for 5 mg/ml of microbeads.

An adhesion rate of 95% was observed eighteen hours after the subculture of the cells and a division number of 2.1.

Similar tests carried out in 250 to 500 ml flasks, with respectively $2.5\times10^5$ cells/ml and $1.8\times10^5$ cells/ml for 5 mg/ml of microbeads give adhesion rates of 98 and 61 and cellular divisions respectively of 2 and 2.47.

These results show clearly that the cells which have grown on these microcarriers of the invention may be reseeded on other carriers, which is of great importance for the development of large-scale cultures.

It will also be noticed that the optimum density obtained in 100 ml culture, which is about $10^6$ cells/ml, is reproducible in culture flasks of larger volume of 250, 500 or 1000 ml, which shows the viability of the microcarriers of the invention.

The whole of the results reported above show that the microbeads of the invention offer surfaces particularly suitable for the culture of normal diploid cells. As already indicated, these cells, which are on the microcarriers, may be infected by a virus or a cellular parasite, which allows the elaboration of different cellular products, particularly viruses suitable for the manufacture of viral vaccines for human use.

What is claimed is:

1. Microparticles comprising particles or beads whose surface at least is formed from a reticulated protein, chosen from protein capable of forming a viscoelastic mass which after reticulation has a fibrous-type structure in a mesh network configuration.

2. The microparticles as claimed in claim 1, having at their surface a charge capacity of about 0.5 to 1.8 meq per gram of dry particles.

3. The microparticles as claimed in claim 2, having at their surface a charge capacity of 0.9 to 1.6 meq per gram of dry particles.

4. The mircoparticles as claimed in claim 2 wherein the functional groups of said reticulation agent not engaged in the reticulation reaction are blocked by fibronectine.

5. The microparticles as claimed in claim 1 wherein the protein is gelatin.

6. The microparticles as claimed in claim 1 wherein the protein is fibronectine.

7. The microparticles as claimed in claim 1 wherein the protein is reticulated with a multifunction agent having at least two aldehyde, azo, sulfonic acid, fluoro groups activated by reactive nitro, imine, azide or chloro groups connected with a cyclic structure whereby the chloro groups are sufficiently active to effect a reticulation reaction with protein.

8. The microparticles as claimed in claim 7, wherein the reticulation agent is glutaraldehyde.

9. The microparticles as claimed in claim 7 or 8 wherein the functional groups of the reticulation agent not engaged in the reticulation reaction are blocked by the protein comprising said microparticles.

10. The microparticles as claimed in claim 7, wherein the functional groups of the reticulation agent not engaged in the reticulation reaction are blocked.

11. The microparticles as claimed in claim 1 wherein said microparticles consist substantially of reticulated protein.

12. The microparticles as claimed in claim 1 wherein said particles are comprised of a surface coating of reticulated protein.

13. The microparticles as claimed in claim 12, wherein the reticulated protein coating is fixed on an anchoring nucleus, comprising chemical groups capable of reacting with the functional groups of the protein of the coating to link therewith, and having a charge capacity of about 0.5 to 1.5 meq per gram of dry particles.

14. The microparticles as claimed in claim 13 wherein the anchoring nucleus is formed of reticulated dextran having tertiary or quaternary amino substituent groups in a proportion such that the charge capacity of the anchoring nucleus particles is about 0.5 to 1.8 meq per gram of dry particles.

15. The microparticles as claimed in claim 13, wherein the anchoring nucleus is formed by reticulated dextran.

16. The microparticles as claimed in claim 1 having at their surface a charge capacity of about $1\pm0.3$ meq per gram of dry particles.

17. The microparticles as claimed in claim 2, 3, 7 or 16 wherein the protein is gelatin.

18. The microparticles as claimed in claim 2, 3, 7 or 16 wherein the protein is gelatin obtained from an alkaline process.

19. The microparticles as claimed in claim 1, 2, 3, or 16, wherein the protein is gelatin and the reticulation agent is glutaraldehyde.

20. The microparticles as claimed in claim 19, wherein the protein is gelatin obtained by an alkaline process.

21. The microparticles as claimed in claim 19, wherein the functional groups of glutaraldehyde not engaged in the reticulation reaction are blocked by gelatin.

22. The microparticles as claimed in claim 2, 3, 7, 8 or 16 in which the protein is fibronectine.

23. The microparticles as claimed in claim 1 wherein the protein is gelatin obtained by an alkaline process.

24. The microparticles as claimed in claim 2, 3, 5, 6, 7, 8, 10, 16 or 23 which consist substantially of reticulated protein.

25. The microparticles as claimed in claim 2, 3, 5, 6, 7, 8, 16 or 23 wherein said microparticles are comprised of a surface coating of the reticulated protein.

26. The microparticles as claimed in claim 1 comprising anchoring nucleus particles comprised of reticulated dextran having tertiary or quaternary amino substituent groups in a proportion such that the charge capacity of the anchoring nucleus particle is about 0.5 to 1.8 meq per gram of dry particles and a surface coating the anchoring nucleus particles comprised of protein reticulated with glutaraldehyde, wherein the protein is selected from gelatin and fibronectine, the functional groups of glutaraldehyde not engaged in the reticulation reaction being blocked by the protein and the microparticles having a charge capacity at their surface of about 0.5 to 1.8 meq per gram of dry particles.

27. The microparticles as claimed in claim 13 or 26 wherein the anchoring nucleus is formed of reticulated dextran having diethylaminoethyl or diethyl-2-hydroxypropylaminoethyl substituent groups in a proportion such that the charge capacity of the anchoring nucleus particle is about 0.9 to 1.6 meq per gram of dry particles and wherein the microparticles have a charge capacity at their surface of about 0.9 to 1.6 meq per gram of dry particles.

28. The microparticles as claimed in claim 14 or 26 wherein the charge capacity of the anchoring nucleus particles and the charge capacity at the surface of the microparticles are about $1\pm0.3$ meq per gram of dry particles.

29. The microparticles as claimed in claim 14 or 26 wherein the reticulated dextran is that commercialized under the trademark Sephadex.

30. In a process for the culture of human diploid cells, comprising forming a suspension of microparticles in a medium suitable for the culture and the growth of the diploid cells, seeding the suspension with normal human diploid cells, subjecting the mixture to incubation under conditions of temperature and duration which allow cellular multiplication and then collecting the cells, the improvement wherein said suspension is comprised of the microparticles as claimed in claim 1, 2, 3, 5, 6, 7, 8, 10, 11, 12, 13, 15, 16, 23, 14 or 26.

31. The process for the culture of human diploid cells as claimed in claim 30, wherein the diploid cells are seeded at the rate of about $10^5$ cells per ml of culture medium containing about 1 to 2 mg, microparticles per ml of culture medium.

32. The process for the culture of human diploid cells as claimed in claim 30 wherein the normal human diploid cells grown on the microparticles are infected with a virus or parasites developing in the human cells for the purpose of preparing antigens of the said virus or said parasites.

33. The process for the culture of human diploid cells in claim 30 wherein the culture medium contains about 1.5 to 1.7 microparticles per ml.

34. The process for the culture of human diploid cells as claimed in claim 30 wherein the culture medium contains about 1.6 mg of microparticles per ml.

35. The process for the culture of human diploid cells as claimed in claim 30 wherein the improvement further comprises prior to forming the suspension, preincubating the microparticles in a culture medium including the elements required for the culture and growth of human diploid cells.

36. The process for the culture of human diploid cells as claimed in claim 35 wherein the improvement further comprises prior to preincubation, washing the microparticles with a buffer solution to eliminate impurities without adversely affecting the surface of the microparticles and sterilizing the microparticles.

37. A process for preparing microparticles or beads useful as microcarriers for the culture of normal human or animal diploid cells or said cells infected by a virus or a cellular parasite comprising contacting particles having a diameter of the order of 40 to 200 $\mu$m, formed of protein capable of forming a viscoelestic mass which after reticulation has a fibrous-type structure in a mesh network configuration, with a solution of a multifunctional reticulation agent to react with the protein, separating the thus reticulated protein particles from the solution of reticulation agent and contacting the reticulated protein particles with said protein to block the functional groups of the reticulation agent not engaged in the reticulation reaction.

38. A process for preparing microparticles or beads useful as microcarriers for the culture of normal human or animal diploid cells or said cells infected by a virus or a cellular parasite comprising contacting a suspension of particles having a diameter of the order of 40 to 200 $\mu$m with a solution of a protein to coat said particles with said protein, wherein said protein is capable of forming a viscoelastic mass which after reticulation has a fibrous-type structure in a mesh network configuration and said particles are formed of material capable of providing an anchoring nucleus for said protein, contacting the protein coated particles with a solution of a multifunctional reticulation agent to react with the protein coating the surface of said particles, separating the particles coated with thus reticulated protein from the solution of reticulation agent and contacting the particles with said protein to block the functional groups of the reticulation agent not engaged in the reticulation reaction.

39. The process as claimed in claim 37 or 38 wherein the surface charge capacity of the final particles is about 0.5 to 1.8 meq of dry particles.

40. The process as claimed in claim 37 or 38 wherein the protein is gelatin.

41. The process as claimed in claim 37 or 38 wherein the protein is gelatin obtained by an alkaline process.

42. The process as claimed in claim 37 or 38 wherein the protein is fibronectine.

43. The process as claimed in claim 37 or 38 wherein the reticulation agent has a least two aldehyde, azo, sulfonic acid, fluoro groups activated by reactive nitro, azide, imine or chloro groups connected with a cyclic structure whereby the chloro groups are sufficiently active to effect a reticulation reaction with protein.

44. The process as claimed in claim 37 or 38 wherein the reticulation agent is glutaraldehyde.

45. The process as claimed in claim 38 wherein the particles providing an anchoring nucleus are comprised of chemical groups capable of reacting with the functional groups of said coating to link therewith and have a charge capacity of about 0.5 to 1.8 meq per gram of dry particles.

46. The process as claimed in claim 38 wherein the particles providing an anchoring nucleus are formed of reticulated dextran.

47. The process as claimed in claim 38 wherein the particles providing an anchoring nucleus are formed of reticulated dextran having tertiary or quaternary amino substituent groups in a proportion such that the charge capacity of the anchoring nucleus particles is about 0.5 to 1.8 meq per gram of dry particles.

48. The process as claimed in claim 38 wherein the particles providing the anchoring nucleus formed of reticulated dextran having diethylaminoethyl or diethyl-2-hydroxypropylaminoethyl substituent groups.

* * * * *